United States Patent [19]
Aulhorn et al.

[11] Patent Number: 5,270,750
[45] Date of Patent: * Dec. 14, 1993

[54] APPARATUS AND METHOD FOR FINDING OF SCOTOMAS IN THE EYE OF A PERSON TESTED

[75] Inventors: Elfriede Aulhorn; Gert Koest, both of Tuebingen, Fed. Rep. of Germany

[73] Assignee: Oculus Optikgeraete GmbH, Wetzlar, Fed. Rep. of Germany

[*] Notice: The portion of the term of this patent subsequent to Oct. 29, 2008 has been disclaimed.

[21] Appl. No.: 846,733

[22] Filed: Mar. 4, 1992

Related U.S. Application Data

[63] Continuation of Ser. No. 689,699, Apr. 19, 1991, abandoned, which is a continuation of Ser. No. 593,291, Oct. 4, 1990, Pat. No. 5,061,060, which is a continuation of Ser. No. 245,417, Sep. 16, 1988, abandoned.

[30] Foreign Application Priority Data

Sep. 18, 1987 [DE] Fed. Rep. of Germany ....... 3731415
Aug. 4, 1988 [EP] European Pat. Off. ......... 88112691.6

[51] Int. Cl.$^5$ ............................................... A61B 3/02
[52] U.S. Cl. ................................... 351/224; 351/243
[58] Field of Search ................. 351/222, 224, 225, 243

[56] References Cited

U.S. PATENT DOCUMENTS 3,883,235 5/1975 Lynn .
4,334,738 6/1982 Seckinger .
4,392,725 7/1983 Sheingorn ............................ 351/224
4,634,243 1/1987 Massof et al. ........................ 351/243
5,061,060 10/1991 Aulhorn et al. ..................... 351/224

FOREIGN PATENT DOCUMENTS 50-25091 3/1975 Japan .
59-120127 7/1984 Japan .
WO85/02103 5/1985 World Int. Prop. O. .

OTHER PUBLICATIONS

Bernhard J. Lachenmayr and Patrick M. O. Vivell, "Perimetrie", Georg Thieme Verlag Stuttgart, New York, 1992, title pages and pp. 325-328.
Article, "Pattern Discrimination Perimetry and Conventional Perimetry in Early Glaucoma Detection", Bruce Drum et al., 5 pages.

Primary Examiner—Bruce Y. Arnold
Assistant Examiner—Hung Xuan Dang
Attorney, Agent, or Firm—Flynn, Thiel, Boutell & Tanis

[57] ABSTRACT

The invention relates to an apparatus and a method for finding blind spots in the eye of a person tested. In examinations carried out to date, it was necessary to scan the entire image field of the person tested. According to the invention an image with a plurality of image points lying closely side-by-side is offered to the person tested, the variations in the brightness of which image points are presented at a high frequency, and additionally, a fixation mark at a defined place. The apparatus and the method can be used in all types of examinations of the field of vision.

16 Claims, 3 Drawing Sheets

APPARATUS AND METHOD FOR FINDING OF SCOTOMAS IN THE EYE OF A PERSON TESTED

This application is a continuation of U.S. Ser. No. 07/689,699, filed Apr. 19, 1991, now abandoned, which is a continuation of U.S. Ser. No. 07/593,291 filed Oct. 4, 1990, now U.S. Pat. No. 5,061,060, which in turn is a continuation of U.S. Ser. No. 07/245,417 filed Sep. 16, 1988, now abandoned.

FIELD OF THE INVENTION

Background of the Invention

The invention relates to a method for finding of visual field defects in the eye of a person tested.

The sensitivity to light variation per retina point is tested during an examination of the field of vision. Two different methods are known, namely, one is known as a kinetic perimetry method, in which the examination is carried out with a moving testing mark, while in the case of the static perimetry method, the sensitivity to the difference in light coming from dark luminous densities is measured exactly at a fixed point. Computer-supported systems are mostly utilized today. These systems operate according to the so-called raster or screening perimetry method. According to one program, a testing-point raster is automatically screened, either with adjusted testing-point brightness or with an exact threshold measurement, the results being then stored and printed out at the end of an examination. Areas, where no recognition or a reduced sensitivity to light variation exists, are marked separately. The earlier the deficiencies are recognized, the more favorable is the prospect for a successful treatment.

Spherical perimeters are mostly used in examinations of the field of vision, in which either the testing point is projected into the sphere through an adjustable projection system or even diode photoconductors or glass fiber photoconductors are mounted in the sphere. These known systems are all rather complicated and mechanically very sensitive, since the highest demands are made on precision.

U.S. Pat. No. 4,634,243 disclose's a method for the examination of the field of vision, in which a flicker pattern image is shown to the person tested. The image contains a regular arrangement of image points in the form of a geometrically constant, limited pattern. This pattern, which is small in comparison to the entire surface of the image, has regularly arranged points of the same density, which differ both from the arrangement and also from the density of the points of the flicker field. To determine visual field defects or similar vision defects, this geometrically arranged dot pattern is moved over the entire image. Thus a scanning of the center field of vision of the volunteer patient up to 30° occurs. Also this method has proven to be disadvantageous, since scanning of the entire field of vision by means of complicated and long lasting examinations is necessary.

A problem in all of these examinations of the field of vision is that the person tested is not able to determine whether or not losses in the field of vision exist. Thus the entire retina must be examined during each examination. The examination could be carried out in a much simpler fashion and in much less time if it were known already at the start of the examination where such field of vision losses are to be expected.

The purpose of the invention is to provide an apparatus and a method for finding scotomas in the eye of a person tested enabling himself or herself to indicate such field of vision losses within a very short period of time.

According to the invention, to the eye of the person tested is thus offered an image on a screen, which consists of a plurality of dots which lie closely side-by-side, the brightness of which dots changes continuously, with the image additionally having a fixation point for the eye. The change in the brightness of the individual image dots can occur regularly or periodically. The simplest apparatus for carrying out the perimetric examinations has proven to be a high-resolution video monitor having a randomly flickering display with a very small grain, similar to a flicker field which results when an interference or breakdown occurs in televisions. The eye of the volunteer patient is spaced a predetermined distance from the video screen with the eye being fixed on a specific fixation point on the image screen. Viewing the flicker field, the person tested can determine within seconds at which areas scotomas exist.

The described abnormal scotomas can be made clearly visible if the patient looks, instead of onto a homogeneous surface, onto a light-dark small grain surface which flickers at a high frequency, similar to the surface of the flicker field on a switched-on television monitor when no program is being received. When the view of the patient is fixed by a clearly visible point fixedly located in the center of the television screen or programmed to be faded in, the visual field defect is sensed as an area which flickers less or not at all, the brightness of which area clearly differing from the surrounding area. The observer can trace the scotoma boundaries with the finder exactly on the television screen. This marking of the patient's own scotomas occurs mostly spontaneously without a special request, because the impression of the limited "cloud" in the flicker field is very impressive for the patient. All recorded absolute scotomas, which have been created through damage to the retina, the optic nerves, the chiasmas or the tractus opticus, can be indicated by the patient in the same manner as done for scotomas or vision losses caused by glaucoma—although it can presently not as yet be recognized when a scotoma is noticed as a lighter and when as a darker cloud. However, in every case the scotoma is noticed by the flickering of the flicker field being in its area sensed not at all or less than in the surrounding area.

A condition facilitating a reproducible noticing of the scotomas by the patient and a quick perimetric control and registration of the noticed field of vision loss is a video monitor on which both a standardized flicker field, produced by a computer and changeable only in its parameters, and also a contourless surface, with freely movable, selectively light or dark testing points, can appear. Furthermore it is advantageous to fade in a field of vision pattern having degree information onto the video monitor to facilitate recognition of the position and expanse of the vision losses.

The noticing of the scotoma in the flicker field can be associated in a very simple manner with a perimetric measuring examination on the screen of the same monitor as a test field. Noticing of the scotoma in the flicker field thus plays the role of a first orienting test, i.e. a screening method whereby within seconds the ophthalmologist is informed whether and where vision losses in the 30 degrees field of vision exist. Subsequently, it is possible to associate in the scotoma area a manual kinetic perimetry of the common type or an automatic raster perimetry. The advantage of such a two-sided method lies in the perimetry measuring having to be carried out only in areas of vision loss which, compared with the present methods, means a considerable savings in time.

The simultaneous use of a high-resolution video monitor both for the flicker field perimetry and also the conventional perimetry permits an exact comparability of the obtained examination results. Contrast, brightness and color can be changed in the same manner in both types of examination. The kinetic and also the static perimetry methods can be carried out either freely movably by hand or, however, also automatically. The type of campimetric procedure can thereby be adjusted completely to the shape and size of the field of vision losses discovered previously with the flicker field perimetry. In this manner, it is possible to relate the advantages of the very quick discovery of scotomas with the exactness of a campimetric method adjusted to the situation.

In dependency on the size of the video monitor results the tested field of vision area. The field of vision area lies at 60 degrees in normal video monitors. The field of vision area can, however, be enlarged by moving the fixation point.

It has been found to be particularly advantageous when the flicker image is projected in a perimeter hemisphere, because it is then possible to carry out the advantages of the double-track perimetric method also in the form of a hemisphere perimetry.

It is particularly advantageous in the inventive apparatus if a brightness adjustment of the image or of the image screen can be carried out at a specific testing or measuring point. This adjustment can occur for example with the help of a photodiode with the current flowing through the photodiode serving as a measurement of the brightness of the image screen. The adjustment can be carried out both continuously during the examination and also at regular intervals. Thus it is possible to adjust and examine precise luminous density graduations in order to achieve reproducible examination results. According to the invention, it is also possible to carry out the luminance threshold at several image points.

It is also possible by means of the inventive apparatus to occupy only those areas of the field of vision with a flicker pattern which have already been identified as areas of vision defects by the person tested. If the remaining image does not show any flickering and the person tested states that the entire image is without a flicker pattern, then the field of vision loss has been proven positively. In order to permit the flicker image to appear only on the predetermined surface portion, the apparatus is provided with a light pen, a mouse or a touch screen.

It is inventively provided to shift or move the image to adjust the fixation point in order to adjust the fixation point to the position of the eye of the person tested. This shifting can be done by means of a computer program with a coordinate system being for example offered to the eye of the person tested. This possibility of adjustment offers the advantage that the conventional complicated apparatus for the fixation and adjustment of the tested person's head can be abandoned. Furthermore, the adjustment of the fixation point can be carried out substantially quicker and simpler.

It is possible according to the invention to change the diameter of the image points in order to permit persons having ametropic eyes to recognize the individual image points. Furthermore, it is possible according to the invention to provide different colors for the image points or color changes to prevent the person tested from adapting the eye to the flicker image. It is furthermore possible to vary the frequency of the change in brightness of the image points in order to make an acclimatization of the patient impossible. With a color change of the image points it is at the same time possible to test the color vision of the person tested.

It is possible by means of the inventive apparatus to verify the position of the scotomas through a positive-negative reversal of the brightness of the individual images.

To make the fixation of the eye of the patient easier, it is possible by means of the inventive apparatus to fade, for example, number series into the computer-controlled image, with the determination of the fixation point being able to occur by the person tested stating which number or which numbers of these series he sees. The fixation of the eye can be controlled by bringing the blind spot of the person tested, at which he sees nothing, into conformity with the fixation point or fixation area. The size of this fixation point or fixation area, that is of an image loss produced by the computer, is smaller than the blind spot itself. The person tested will thus already during a small change of the fixation of the eye be able to immediately determine a change.

A further advantage of the inventive apparatus lies in a plurality of finely graduated gray values being able to be illustrated in on the image, for example, when using a common television screen having 256 gray values. It is thus particularly easy to carry out threshold measurements.

A particularly favorable further development of the inventive apparatus exists in giving the treating person, for example the physician, a second screen, so that he will at any time be informed regarding the position and size of the respective fields of loss.

It has proven to be particularly advantageous with respect to the inventive method to effect, for the purpose of an early recognition of glaucoma, an artificial increase of the pressure on the eye of the person tested. This may be done for example through a suction pump or through medication. It is possible in this manner to predetermine the vision defects which would occur during a natural change of the pressure on the eye.

The capability of easily noticing one's own field of vision losses in the flicker field has still further advantages. It enables interested patients to themselves control their scotomas at home at the television screen. They only must be informed that they must keep at all times the same distance from the screen (approximately 30 cm.), that they must cover one eye and that furthermore a still fixation with the help of a fixation point must be assured. A possible enlargement of the blind spot or the occurrence of new scotoma areas can then be discovered by well observing patients at home using their own television set.

BRIEF DESCRIPTION OF THE DRAWINGS

The invention will be described hereinbelow and with reference to one exemplary embodiment illustrated in the drawings with further advantages of the invention resulting from this description.

In the drawings.

DETAILED DESCRIPTION

Figure 1:
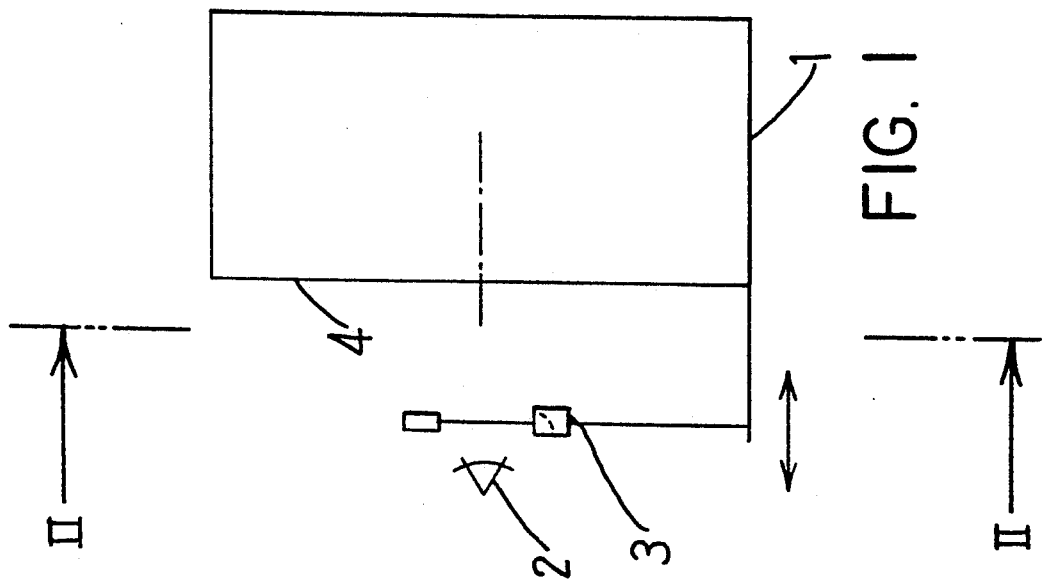
FIG. 1 is a schematic side view of one exemplary embodiment of the inventive apparatus.

A video monitor 1 is illustrated in a side view in FIG. 1. A chin support 3 is used to create an exact and defined but changeable distance between the eyes 2 of a volunteer patient and the video monitor 1. The chin support 3 is arranged at a distance from the screen 4 of the video monitor 1, so that the area of the field of vision to be examined has an approximate range of 60 degrees.

Figure 2:
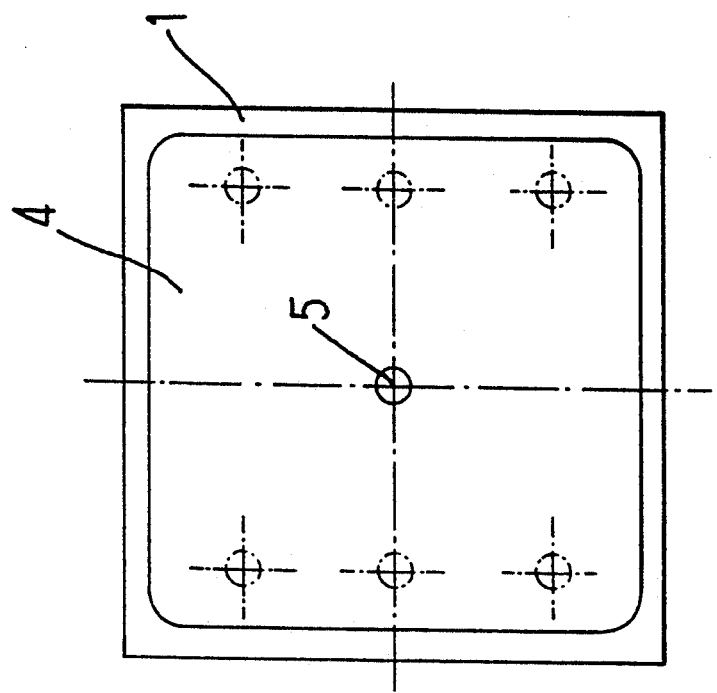
FIG. 2 is a cross-sectional view taken along the line II—II of FIG. 1.

FIG. 2, which is a front view of the screen 4, shows a fixation point 5 usually arranged in the center of the screen. However, this fixation point can be shifted laterally and elevationally so that the area of the field of vision can be shifted toward the edge and thus can be enlarged. A shifting of the fixation point is not necessary if the video monitor is of such a size that the entire field of vision of the person tested can be covered.

It has been found during a practical use that scotomas can be recognized best if the flicker field is presented with a high flicker frequency, high contrasts and a small grain. Most examinations were for this reason carried out at a frequency of 50 Hz, a luminous density of 60 cd./m.$^2$ of the bright elements and 0.8 cd./m.$^2$ of the dark elements. The relationship between the dark and the bright elements was 50% or 70% in favor of the dark elements. The elements have a size of 15 angular minutes in the form of small squares.

The head of the patient is, in the arrangement illustrated in FIG. 1, spaced approximately 30 cm. from the monitor. The test field of the monitor, for example, is 25 by 38 cm. in size, so that a cut-out of the field of vision of approximately 35 degrees in the horizontal and approximately 24 degrees in the vertical results. It is possible by means of the inventive apparatus to fade in a polar coordinate system with circles in a 5 degrees visual angle distance on the monitor. According to the invention it is possible not only for the flicker image and the polar coordinate pattern to appear on the test field, but also to create a homogeneous field for the common perimetry. This field can be offered in various luminous densities between 60 and 0.8 cd./m.$^2$.

Figure 3A:
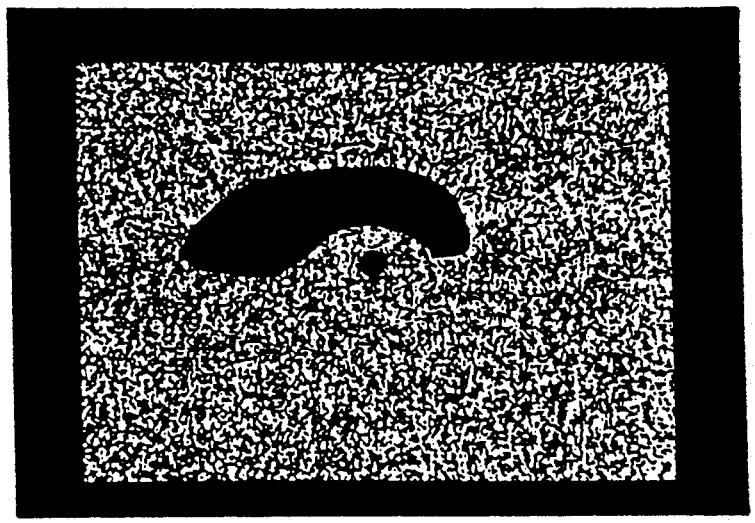
FIGS. 3A-3C illustrates the practical procedural steps followed during an examination.
Figure 3B:
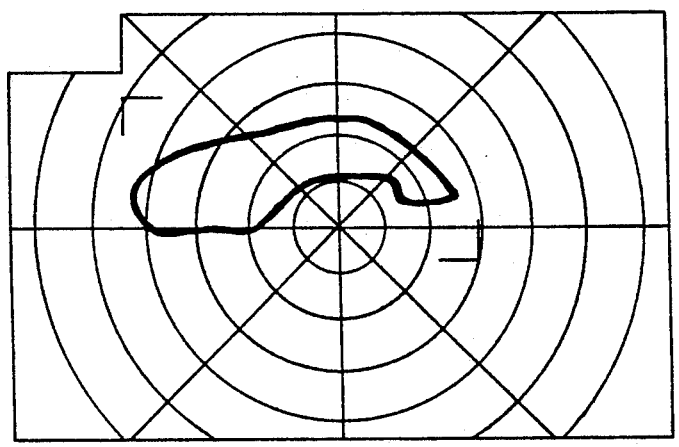
Figure 3C:
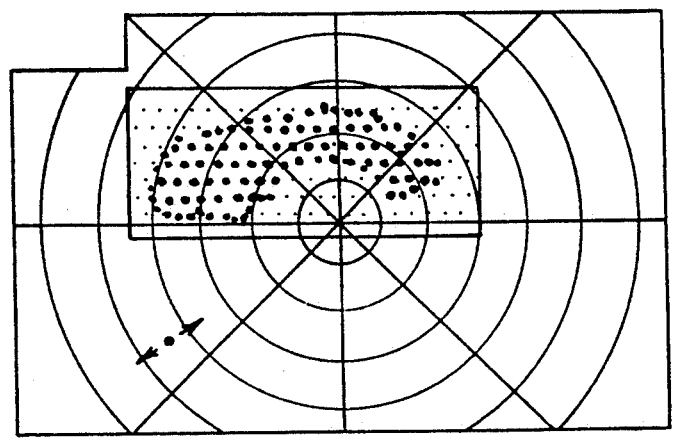

An inventive examination procedure will be described hereinbelow with reference to FIGS. 3a, 3b and 3c. The examination starts with a showing of the flicker field on the monitor (FIG. 3a). The distribution and/or brightness of the image points of the flicker field can be varied according to a random function or program. After the eye of the person tested is fixed on the fixation point illustrated in the center of the image, the patient can very quickly show the blind-spot area to the physician. The physician can thereafter, for example by means of a mouse, fade the visual defect area into the flicker field, as this is illustrated in FIG. 3a. A polar coordinate pattern is subsequently shown on the image, in which, as is illustrated in FIG. 3b, the scotoma area is shown. It is subsequently possible to further examine this area with the static or kinetic perimetry methods on a homogeneous background. The physician moves during the kinetic perimetry method the testing point, for example by means of the mouse, freely over the monitor (3c), such that field of vision losses can be indicated by the person tested pressing a key. This procedure is illustrated on the lower half of the picture in FIG. 3c. The static perimetry method occurs automatically as in a raster perimetry, with the testing points, as illustrated in the upper half of the picture in FIG. 3c, being offered by way of random distribution in the preselected field. The person tested thus acknowledges the seen image points by pressing down a key.

The method according to the invention creates an excellent screening procedure for facilitating a subsequent examination with the same monitor and with a quantitatively measuring perimetry to selectively investigate only the pathological areas in the field of vision. This significantly reduces the examination time compared with any conventional method.

A further advantage is the easy and effortless performance of the method. Physician and patient sit side-by-side and together view the monitor screen on which one after the other or in any desired sequence the flicker field, the polar coordinate system and the perimetry field can appear. By this new method the field of vision examination loses the character of an exhausting, and bothersome trial. The patient no longer experiences a stress situation.

Figure 4:
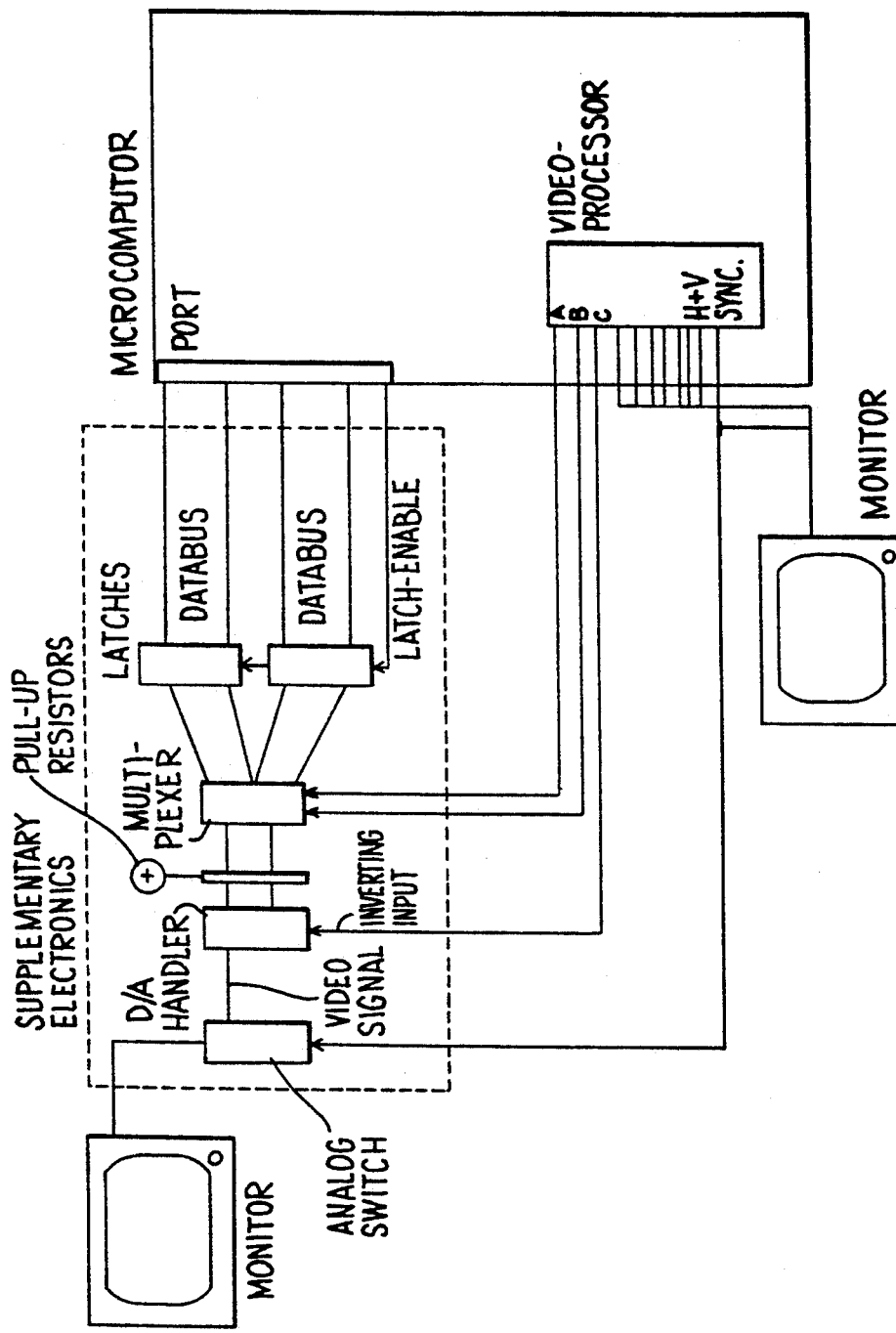
FIG. 4 is a schematic illustration of an apparatus for producing a video image for the threshold perimetry.

FIG. 4 illustrates an apparatus for producing a video image, suited for threshold perimetry, out of the video signals of a microcomputer.

It has been recognized that for a video image, suited for threshold perimetry, only two finely graduated gray values, namely for the background and for the testing point are needed, and a selectively black or white fixation symbol. An image suited for threshold perimetry can be produced with simple means out of four TTL-video signals using supplementary electronics for a microcomputer. The condition for this is that the microcomputer delivers a digital video signal consisting of more than 3 bits. The advantage of this method consists in the possibility of producing a further black-white image with the remaining video signals of the computer, for example on a second observation monitor.

The two graduatable gray values are stored as digital values (databus 8 or more bits, depending on the required number of gray stages) by the microcomputer in electronic latches. The microcomputer provides furthermore four TTL-outputs from its video processor. A multiplexer can be switched by a first one of the TTL-signals (A). The multiplexer places each one of the electronic registers on a digital-analogue converter (D/A converter). Thus, it is possible to produce out of a binary image, which is produced by a microcomputer and relies on the respective video outputs, a video image which is very significantly variable in its gray values.

A second TTL-signal (B) can switch the multiplexer tristate, so that pull-up resistors, which are provided at the input of the digital-analogue-converter, apply the maximum digital word to the converter. It is possible with the help of this second TTL-signal (B) to fade in a fixation symbol, the gray value of which corresponds with the highest digital input value of the digital-analogue converter.

If the fixation symbol is to correspond with the minimal digital value, this is made possible with the help of a third TTL-signal (C) controlling an inverting bit existing in the digital-analogue-converter. Thus it is possible to illustrate a fixation symbol corresponding to the minimal digital value.

The digital-analogue converter delivers an analogue signal to which, with the help of an analogue switch, the necessary video synchronization impulses can be admixed. The impulses are also taken over by the host calculator of the video processor as a fourth TTL-signal (D).

The microcomputer and associated electronic circuit of FIG. 4 thus constitute an image generating arrangement capable of displaying on the screen of one of the illustrated monitors a television image which includes a fixation point and includes a plurality of image points that vary dynamically in brightness.

We claim:

1. In a method for finding visual field defects in the eye of a person tested, the improvement comprising the steps of offering to the eye of the person tested, which eye is at a pregiven distance from a screen, an image on the screen which includes a plurality of image points lying closely side-by-side, the brightness of the image points changing randomly and continuously at a frequency causing an eye under test which has a visual field defect to substantially instantaneously observe in its entirety a region of said image which corresponds to the defect and within which the brightness of the image points appears to the eye to be substantially static, and offering a fixation point for the eye so that a line of sight of the eye is directed toward the screen.

2. The method according to claim 1, wherein the brightness and the brightness variations of the individual image points is adjustably controlled.

3. The method according to claim 1, wherein a reproducible flicker pattern is offered to the person tested, which flicker pattern has more dark portions than light portions.

4. The method according to claim 1, wherein dark testing points on a light background or light testing points on a dark background or colored testing points can in addition be produced and, if desired, moved on the television screen to carry out static or kinetic perimetry.

5. The method according to claim 4, wherein when using a flat screen the testing points can be adjusted in size and/or brightness depending on the position on the television screen in order to create the same conditions as in a sphere.

6. The method according to claim 1, wherein the flicker field is projected in a sphere.

7. The method according to claim 1, wherein the values found on the television screen are stored and, if desired, are printed out.

8. The method according to claim 1, wherein a field of vision pattern with degree information is faded in on the television screen.

9. The method according to claim 1, wherein the method is carried out during the time that the internal eye pressure of the eye of the person tested is increased.

10. The method according to claim 1, wherein the testing point information illustrated on the television screen is converted and adjusted each time depending on the variable distance that the examined eye is from the television screen.

11. The method according to claim 1, wherein the brightness variations are presented to the person tested on a single colored or multi-colored background on the television screen.

12. In a method for finding visual field defects in the eye of a person tested, the improvement comprising the steps of offering to the eye of the person tested, which eye is at a pregiven distance from a screen, an image on the screen which includes a plurality of image points lying closely side-by-side, the brightness of the image points changing continuously at a frequency causing an eye under test which has a visual field defect to substantially instantaneously observe in its entirely a region of said image which corresponds to the defect and within which the brightness of the image points appears to the eye to be substantially static, and offering a fixation point for the eye so that a line of sight of the eye is directed toward the screen; wherein the eye of the person tested is detected with a camera and the position of the eye is illustrated on a control monitor with fading in of cross lines.

13. In an apparatus for finding of visual field defects in the eye of a person tested, including a screen producing an image, the improvement comprising image generating means for displaying television imagery on said screen which includes a plurality of closely positioned side-by-side lying black/white or colored image points, for subjecting the brightness of said image points to high frequency variations, and for displaying on said screen a fixation point at a predetermined location to which a line of sight of an eye under test is to be directed, said image generating means including control means for controlling the imagery and the brightness of the image points so that an eye under test which has a visual field defect will substantially instantaneously observe in its entirety a region of said image which corresponds to the defect and within which the imagery and brightness of said image points appears to the eye to be substantially static.

14. The apparatus according to claim 13, wherein each said image point has a size of approximately 15 angular minutes.

15. An apparatus for testing an eye for visual field defects, comprising: a visually observable screen; means for defining a fixation point for an eye under test so that a line of sight of the eye is directed toward said screen; and means for displaying on said screen an image including a plurality of closely positioned points which flicker in brightness independently of each other at a frequency causing an eye under test which has a visual field defect to substantially instantaneously observe in its entirety a region of said image which corresponds to the defect and in which the brightness of said points appears to the eye to be substantially static.

16. An apparatus for testing an eye for visual field defects, comprising: a visually observable screen; means for defining a fixation point for an eye under test so that a line of sight of the eye is directed toward said screen; an means for displaying on said screen a defect detecting image which is invisible to portions of an eye having visual field defects, said defect detecting image including a plurality of closely positioned points which flicker in brightness at a frequency causing an eye under test which has a visual field defect to substantially instantaneously observe in tis entirety a region of said image which corresponds to the defect and within which the brightness of said points appears to the eye to be substantially static.

* * * * *

UNITED STATES PATENT AND TRADEMARK OFFICE
CERTIFICATE OF CORRECTION

PATENT NO. : 5,270,750
DATED : December 14, 1993
INVENTOR(S) : Elfriede AULHORN et al It is certified that error appears in the above-identified patent and that said Letters Patent is hereby corrected as shown below:

Column 8, line 57; change "an" to ---and---.

Signed and Sealed this

Twenty-fourth Day of May, 1994

Attest:

BRUCE LEHMAN

Attesting Officer     Commissioner of Patents and Trademarks